United States Patent [19]
Kalinich

[11] Patent Number: 6,107,098
[45] Date of Patent: Aug. 22, 2000

[54] URANIUM-CONTAINING/METAL BINDING COMPLEX, PROCESS OF MAKING AND METHOD OF USE FOR THE DETERMINATION OF NATURAL, AND DEPLETED URANIUM IN BIOLOGICAL SAMPLES

[75] Inventor: John F. Kalinich, Silver Spring, Md.

[73] Assignee: The United States of America as represented by the Secretary of the Army, Washington, D.C.

[21] Appl. No.: 09/032,400

[22] Filed: Feb. 27, 1998

[51] Int. Cl.[7] .................................................... G01N 33/20
[52] U.S. Cl. .............................. 436/74; 436/73; 436/80; 436/81; 436/166; 422/61
[58] Field of Search ........................ 436/73, 74, 81–82, 436/166; 422/61, 80

[56] References Cited

PUBLICATIONS

D.A. Johnson et al. *Anal. Chim. Acta* 1971, 53, 73–79.
P. Pakalns et al. *Anal. Chim. Acta* 1972, 62, 207–209.
D.A. Johnson et al. *Talanta* 1975, 22, 253–265.
T. Wu et al. *Fenxi Huaxue* 1982, 10, 235–237.
S.–C. Hung et al. *Talanta* 1982, 29, 629–631.
K. Ohshita et al. *Anal. Chim. Acta* 1983, 149, 269–279.
T.P. Lynch et al. *Analyst* 1983, 108, 470–475.
C. Silfwerbrand–Lindh et al. *Anal. Chim. Acta* 1984, 160, 11–19.
E.A. Jones *Anal. Chim. Acta* 1985, 169, 109–115.
X. Li et al. *Youkuangye* 1985, 4, 59–62.
I. Brcic et al. *Millcrochim. Acta* 1985, 2, 187–193.
Q. Xu et al. *Chem. Abstr.* 1985, 103, 204989j.
D. Horiguchi et al. *Chem. Abstr.* 1986, 104, 218205h.
L. Ding *Fenxi Huaxue* 1987, 15, 71–73.
B. Xia et al. *Youkuangye* 1987, 6, 33–37.
H. Chen et al. *Youkuangye* 1988, 7, 56–58.
H. Liu *Fenxi Shiyianshi* 1988, 7, 56.
L. Sommer et al. *Can. J. Chem.* 1988, 66, 401–405.
L. Dai *Lihua Jianyan, Huaxue Fence* 1989, 25, 209–210.
A. M. S. Abdennabi *Arabian J. Sci. Eng.* 1990, 15, 473–478.
K. Ohzeki et al. *Chem. Abstr.* 1992, 116, 200733s.
B. Xia et al. *Youkaungye* 1993, 12, 38–45 & 50.
M. E. F. Lae Spada et al. *Analyst* 1993, 118, 209–212.
L. Sun *Youkuangye* 1993, 12, 276–279.
I. Othman *Chem. Abstr.* 1993, 118, 250750g.

*Primary Examiner*—Arlen Soderquist
*Attorney, Agent, or Firm*—Werten F.W. Bellamy

[57] ABSTRACT

A uranium-containing/metal binding complex and process for the determination of natural and depleted uranium in biological samples such as water, urine, blood serum, saliva, amniotic fluid, cerebrospinal fluid, sweat, stool extract, synovial fluid, tears, semen extract, sputum, and peritoneal fluid. The samples are mixed with a buffer, one or more masking agents, and a solubilizing compound, to form a uranium-containing metal binding complex composition, followed by the addition of a pyridylazo indicator dye to said composition. The increase in absorbance due to the uranium-dye complex is determined with a spectrophotometer or colorimeter.

17 Claims, 6 Drawing Sheets

2-(5-Bromo-2-pyridylazo)-5-diethylaminophenol
[Br-PADAP]

6,107,098

URANIUM-CONTAINING/METAL BINDING COMPLEX, PROCESS OF MAKING AND METHOD OF USE FOR THE DETERMINATION OF NATURAL, AND DEPLETED URANIUM IN BIOLOGICAL SAMPLES

GOVERNMENT INTEREST

This invention described herein may be manufactured, licensed and used by or for the U.S. Government without the payment of any royalties thereon. The U.S. Government has a nonexclusive, nontransferable, irrevocable, paid-up license to practice or have practiced for or on behalf of the Government any aspect of the subject invention.

TECHNICAL FIELD OF THE INVENTION

This invention relates to the field of detecting and quantitatively measuring the amount of natural and/or depleted uranium in biological fluids. More specifically, it is in the field of detecting uranium, formulating uranium-containing/metal binding complex compositions and the use of said compositions.

BACKGROUND OF THE INVENTION

Naturally occurring uranium primarily consists of three isotopes in the following percentages (by weight): $^{238}$U 99.283%; $^{235}$U 0.711%; and $^{234}$U 0.005%. Enriched uranium, produced for nuclear power generation and weapons manufacture, contains greater then 0.711% $^{235}$U. Uranium containing less than 0.711% $^{235}$U is considered "depleted" uranium. Depleted uranium usually contains less than 0.3% $^{235}$U and is therefore less than half as radioactive as natural uranium. Because it is extremely dense, depleted uranium has several applications including the armor plating of military vehicles. It is also used in armor piercing munitions that were first used extensively in the Persian Gulf War. Unfortunately several military personnel were injured with internalized depleted uranium particles in this conflict. This was a medical concern because of the known health risks associated with enriched uranium. Research shows that internalized uranium is eliminated from the body in the urine via the kidneys (H. C. Hodge, Uranium, Plutonium, Transplutonic Elements: Handbook of Experimental Pharmacology, Springer-Verlag, Berlin, Vol 36 (1973), pp. 5–68). However, at the time, there was not a rapid and convenient method to measure depleted (or natural) uranium in biological fluids (urine in particular) that was suitable for a battlefield situation. Rapid assessment of the presence of depleted uranium in injuries is necessary for proper treatment decisions.

Previous art shows a variety of techniques for the measurement of uranium in biological fluids. Chakavarti and colleagues (1980, Int. J. Appl. Radiat. Isotop., 31, pp. 793–795) teach that the amount of $^{235}$U in urine can be determined by the fission track etch technique. This technique was improved on by Ide et al. (1979, Health Phys., 37, pp. 405–408) and called the delayed neutron emission method. Addition advancements in this area led to the technique of neutron activation analysis (1992, H. S. Dang, V. R. Pullat, and K. C. Pillai, Radiat. Protect. Dosim., 40, pp. 195–197). While these techniques are sensitive, they require extensive, labor-intensive sample preparation, as well as a nuclear reactor to provide the thermal neutrons needed for sample activation.

U.S. Pat. No. 4,198,568 to Robbins and Kinrade (1980) discloses that uranium determination in aqueous samples is achieved by ultraviolet light-induced phosphorescence of the uranium. Zook, Collins, and Pietri teach that uranium in biological samples can be determined by the method of pulsed laser-induced fluorescence (1981, Mikrochem. Acta, II, pp. 457–468). After further technical improvements (1992, R. Brina and A. G. Miller, Analyt. Chem., 64, pp. 1413–1418), the method of laser-induced kinetic phosphorimetry was developed (1995, R. Brina, American Laboratory, May, pp. 43–47). However, these methods are hindered by the presence of quenching substances in the sample (1989, E. S. Gladney, W. Moss, M. A. Gautier, and M. G. Bell, Health Phys., 57, pp. 171–175). This results in lower sensitivity or a requirement for extensive sample preparation before analysis. In addition, the instrumentation necessary for these analyses severely restricts their use in a field situation.

The technique of inductively coupled plasma mass spectrometry is also used to determine uranium content in biological samples (1989, E. S. Gladney, et al., Health Phys., 57, pp. 171–175; 1996, Z. Karpas, et al., Health Phys., 71, pp. 879–885). Goldstein and coworkers (1997, Health Phys., 72, pp. 10–18), as well as McKibbin (U.S. Pat. No. 5,190, 881), teach that alpha-spectrometry can also be used to measure uranium content in biological fluids. However, inductively coupled plasma mass spectrometry requires instrumentation that would be difficult to maintain in a field situation and the technique of alpha-spectrometry is hindered by the extensive sample preparation time needed.

For use in the field, spectrophotometric or colorimetric detection methods are preferable. Fitoussi, Lours, and Musikas (U.S. Pat. No. 4,349,350) teach that uranium in an organic solvent can be added to a mixture of a neutral organophosphorus compound and a dialkyl dithiophosphoric acid. This results in a complex whose optical density can be determined at 390 nm. While this application can be used to determine uranium levels from organic extracts obtained from the reprocessing of nuclear fuels, there is no indication that it can be used for biological fluids such as urine. Furthermore, considering the extensive sample preparation required, this method could not be conveniently used in a field situation. That is also the case for the dye arsenazo III which has been described for uranium determination in organic-solvent extracts of samples (L. C. Baylor and S. M. Stephens, U.S. Pat. No. 4,424,211) and reversed-phase column chromatographically purified geological samples (1988, X. Wu and W. Qi, Analyt. Chim. Acta 214, 279–288). The stain 2-(5-bromo-2-pyridylazo)-5-diethylaminophenol has been used to detect uranium in organic solvent-extracted geological samples (1971, D. A. Johnson and T. M. Florence, Analyt. Chim. Acta 53, 73–79; 1972, P. Palkalns and B. R. McAllister, Analyt. Chim. Acta 62, 207–209) or kerosene-diluted uranium leach liquors from nuclear fuel reprocessing facilities (1979, S. J. Lyle and M. Tamizi, Analyt. Chim. Acta 108, 267–275; 1985, E. A. Jones, Analyt. Chim. Acta 169, 109–115; 1990, S. D. Hartenstein, Analyt. Chim. Acta 228, 279–285). These methods have never been tested with uranium-containing biological samples, such as urine. They also require extensive sample preparation before the uranium levels can be determined. In addition, extraction of biological samples with organic solvents of the type used for geological samples would result in phase separation. Because any uranium in a biological sample could be bound to lipids (1969, D. O. Shah, J. Colloid Interface Sci. 29, 210–215) and proteins (1995, B. Volesky and Z. R. Holan, Biotechnol. Prog. 11, 235–250), as well as to inorganic components, organic extraction of the biological sample would partition the uranium between the organic and aqueous phases. Organic solvents also cause the precipitation of proteins. Therefore organic extraction of a protein-containing biological sample would result in three components: an organic phase, an aqueous phase, and a protein precipitate. All three of these components are capable of containing significant amounts of uranium. Thus, for an accurate determination of the total amount of uranium present in the sample, all three components (organic phase, aqueous phase and protein phase) would have to be analyzed. Therefore, the application of the current methods of uranium (depleted or natural) determination to a battlefield situation is severely hindered by one or both of the following factors:

(a) Extensive sample preparation is required before analysis. Extraction into organic solvents, column purification, and acid-digestion of samples at high temperatures are examples of some of the preparatory procedures necessary for current uranium detection methods.

(b) Many of the uranium determination procedures need elaborate instrumentation. Nuclear reactors, inductively coupled plasma mass spectrometers, and laser-induced kinetic phosphorimetric analyzers are not commonly found in battlefield medical facilities.

SUMMARY OF THE INVENTION

Surprisingly, in accordance with the present invention, applicant has discovered a uranium-containing/metal binding complex composition, the process of making the same and its use for the determination of natural or depleted uranium in biological fluids. The practice of this invention involves a biological sample, which may contain uranium, one or more masking agents, buffer, a solubilizing agent, and an indicator dye. The increase in absorbance as a result of the uranium-dye complex produced in accordance with this invention is determined with a spectrophotometer or colorimeter. It is accordingly one object of the present invention to provide uranium-containing/metal binding complex compositions wherein its uranium metal components demonstrate a preferential reactivity with pyridylazo indicator dye compounds.

Additionally objects of the invention are:

(a) to provide a process for the detection of uranium, both natural or depleted, in biological fluids including, but not limited to, water, urine, blood serum, saliva, amniotic fluid, cerebrospinal fluid, sweat, stool extract, synovial fluid, tears, semen extract, sputum, and peritoneal fluid;

(b) to provide a process for uranium determination that can be conducted rapidly and accurately;

(c) to provide a process for uranium determination that does not require extensive sample preparation before analysis;

(d) to provide a process for uranium determination that does not require the use of complicated instrumentation;

(e) to provide a process for uranium determination that requires only a visible-range spectrophotometer or colorimeter for instrumentation;

(f) to provide a process for uranium determination that can be used in a battlefield situation; and (g) to provide a process for uranium determination that requires little or no technical training to conduct.

Other objects and advantages of the present invention will become apparent as the description thereof proceeds.

BRIEF DESCRIPTION OF THE DRAWINGS AND TABLES

A better understanding of this invention and its advantages over other uranium detection methods will be readily apparent by referring to the following detailed description of the invention in conjunction with the figures and tables herein:

FIGURES

TABLES

Table 1 shows the metals which do not interfere with the determination of uranium and those which can be successfully masked so that their interference can be eliminated.

Table 2 shows the effect of temperature on my process for uranium determination in biological fluids.

DETAILED DESCRIPTION OF THE INVENTION

Figure 1:
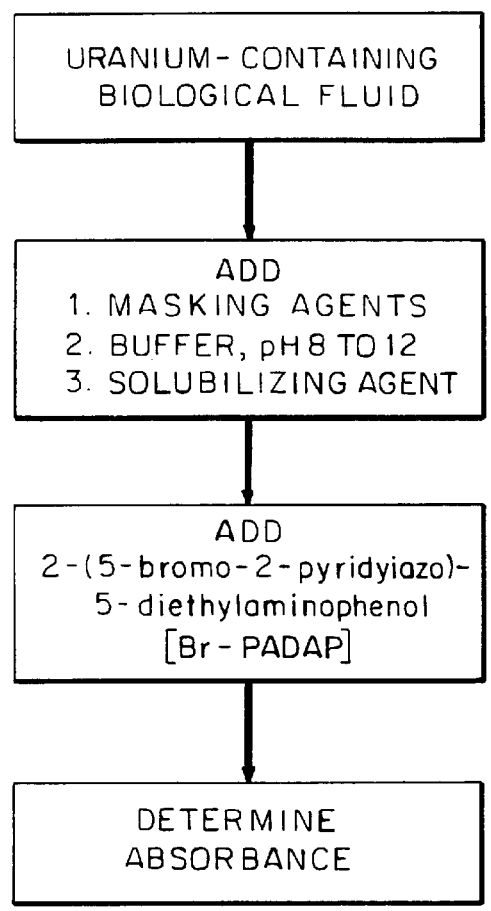
FIG. 1 shows a flowchart of the process for the determination of uranium in biological fluids.

The method of this invention, as shown schematically in FIG. 1, consists of adding the following to an uranium-containing biological fluid: one or more masking agents, a physiological buffer, a solubilizing agent, and a pyridylazo indicator dye capable of preferentially binding uranium under these conditions, despite the presence of other metals. After allowing an appropriate amount of time for color development, the absorbance of the mixture is determined in a spectrophotometer or colorimeter. The amount of absorbance increases as the uranium content of the biological fluid sample increases. The exact concentration of uranium in the sample can be calculated by using a standard curve. Specific examples representative of the general applicability of this method will be presented later in this description.

The masking agents, which bind to metals, are used to prevent the reaction between the indicator dye and any endogenous metals present in the biological fluid sample. These are preferred sodium citrate, ethylenediamine tetraacetic acid (EDTA), cyanide, and thiourea. Many metals do not interact with the selected indicator dye and these are listed in Table 1. Other metals can react with the indicator dye, but the interaction between metal and indicator dye can be prevented by the use of masking agents. These metals are also listed in Table 1. The indicator dye having a stronger affinity to uranium than to other metals and the use of masking agents negates any interference by practically all biologically relevant metals. The use of a mixture of sodium citrate and EDTA, both at a final concentration of 10 mM, works well in this regard and avoids the use of a potentially hazardous substance (cyanide).

The physiological buffer may include, but is not limited to, 3-[cyclohexylamino]-1-propanesulfonic acid (CAPS), borate, or tris(hydroxymethyl)aminomethane (Tris). The reaction of the indicator dye with the uranium is a pH-dependent process. At a pH below approximately 7.0, very little color development is observed. In addition, at a pH greater than 12, a linear absorbance response is not seen between the indicator dye and the uranium. This may be the result of a partial hydrolysis of the indicator dye due to the high pH levels. A pH range between 8 and 12 works well, although not all buffers in this range can be utilized. For example, carbonate, malate, bicarbonate, and phosphate buffers interfere with the interaction of the indicator dye and the uranium and therefore cannot be used in the process. Although the final concentration of the buffer in the reaction mixture can be varied, the addition of 3-[cyclohexylamino]-1-propanesulfonic acid (CAPS, pH 11), to a final concentration of 100 mM, provides sufficient buffering capacity to keep the pH level within an acceptable range.

The solubilizing agent prevents the assay components and biological sample from forming a flocculent compound and precipitating out of solution. The use of a solubilizing agent also negates the need for extensive pretreatment of the biological fluid sample before being assayed for uranium content. The solubilizing agent can be chosen from, but is not limited to, quaternary ammonium salt compounds such as ethylhexadecyldimethylammonium bromide. The final concentration of the solubilizing agent in the reaction mixture can be varied. Ethylhexadecyldimethylammonium bromide at a final concentration of 1% works well as a solubilizing agent. In addition, the solubilizing agent (ethylhexadecyldimethylammonium bromide), masking agents (citrate and EDTA), and physiological buffer (CAPS, pH 11) can be combined in a concentrated stock solution to minimize the number of manipulations required for the process.

Figure 2:
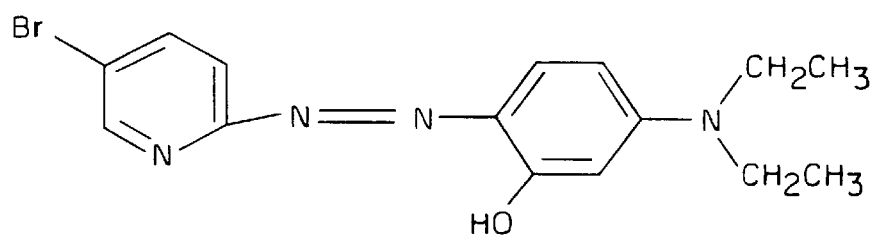
FIG. 2 shows the chemical structure of 2-(5-bromo-2-pyridylazo)-5-diethylaminophenol.

Under these conditions, a preferred indicator dye suited for uranium detection is one of the pyridylazo compounds such as 2-(5-bromo-2-pyridylazo)-5-diethylaminophenol [Br-PADAP]. FIG. 2 shows the chemical structure of 2-(5-bromo-2-pyridylazo)-5-diethylaminophenol. The Br-PADAP is prepared as a concentrated stock solution in 9 parts of 100% ethanol and 1 part of 1M KOH. The ethanol/KOH solvent system can be varied, as persons of skill in the art will appreciate. The Br-PADAP is added to the uranium-containing biological fluid sample after the addition of solubilizing agent, masking agent, and buffer. Br-PADAP is preferably added to a final concentration of between about 1 and 1000 micromolar, most preferably about 10 micromolar.

Figure 3:
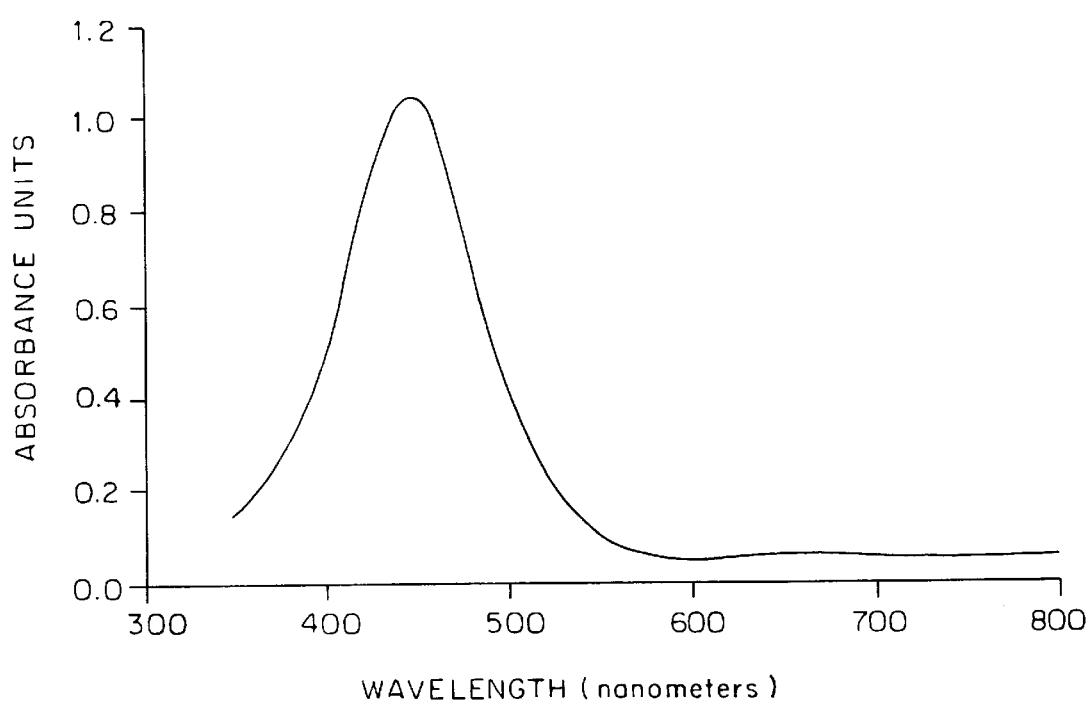
FIG. 3 shows the absorption spectrum for 2-(5-bromo-2-pyridylazo)-5-diethylaminophenol.
Figure 4:
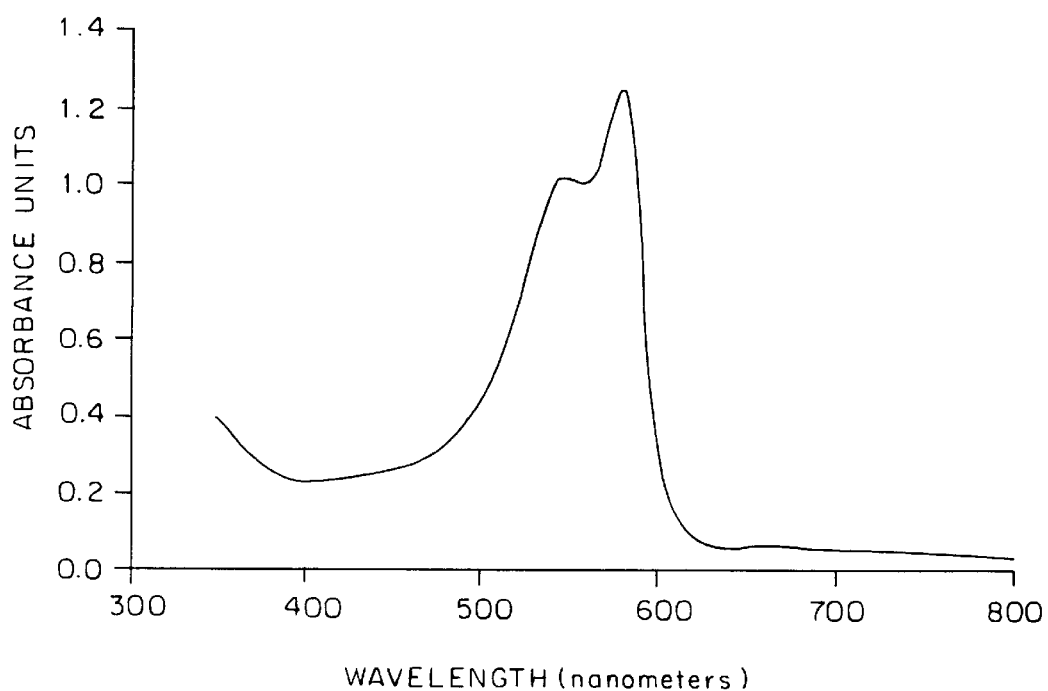
FIG. 4 shows the absorption spectrum for the 2-(5-bromo-2-pyridylazo)-5-diethylaminophenol-uranium complex.

After an appropriate amount of time to allow for color development, the absorbance of the assay mixture is read in a spectrophotometer or colorimeter. The absorption maximum for Br-PADAP, in the absence of uranium, is at approximately 444 nanometers as shown in FIG. 3. When uranium is present, Br-PADAP binds to the metal to form a Br-PADAP-uranium complex. The Br-PADAP-uranium complex shows an absorption maximum at approximately 578 nanometers, although this can vary depending on the sample. As shown in FIG. 4, the absorption peak is very broad. Because of the broadness of the absorption peak, the absorbance of the Br-PADAP-uranium complex can be measured at one of several wavelengths and an accurate determination of uranium content can still be made. Since the Br-PADAP-uranium complex absorbs in the visible range, measurements can be made with a simple visible-light spectrophotometer or colorimeter rather than with a more complicated instrument.

More precisely, applicant has discovered uranium-containing/metal binding compositions, process for making and using the same, including its inclusion in a diagnostic kit, with the following attendant itemized features:

A specific working example is presented below to illustrate in general the practice of this invention but should not be considered as a limitation thereof.

Features

What is Featured is:

1. A uranium-containing/metal binding complex composition wherein the uranium metal component of said composition demonstrates a preferential reactivity with a pyridylazo indicator dye compound to form a uranium-pyridylazo complex.
2. A composition according to Feature 1 wherein the metal binding composition consists of masking agent(s), a buffer capable of maintaining the pH at between 8 and 12, and a solubilizing agent.
3. A composition according to Feature 2 wherein the metal binding masking agent(s) is selected from the group consisting of sodium citrate, ethylene diamine tetraacetic acid (EDTA), cyanide, thiourea, and mixtures thereof.
4. A composition according to Feature 3 wherein the metal binding masking agent(s) is a mixture of sodium citrate and ethylene diamine tetraacetic acid.
5. A composition according to Feature 4 wherein the pyridylazo indicator dye compound is 2-(5-bromo-2-pyridylazo)-5-diethylaminophenol.
6. A method for the detection of uranium in biological fluid specimens which comprises the steps of (1) contacting the biological fluid specimens which may contain uranium with a mixture of metal binding masking agent(s); buffer agent(s),capable of maintaining the pH at between 8 and 12; and a solubilizing compound to produce a uranium-containing/metal binding complex; (2) adding a pyridylazo indicator dye compound to the complexes produced in step (1); and (3) measuring the formation of uranium-pyridylazo complex with a visible-light spectrophotometer or colorimeter and (4) relating the measurements of step (3) to the presence of or concentration of uranium in biological fluid specimens.
7. A method according to Feature 6 wherein the pyridylazo indicator dye compound is 2-(5-bromo-2-pyridylazo)-5-diethylaminophenol.
8. A method according to Feature 7 wherein the concentration of the indicator dye is between about 1 and 1000 micromolar.
9. A method according to Feature 8 wherein the concentration of the indicator dye is about 10 micromolar.
10. The method of Feature 9 wherein said masking agents are selected from the group consisting of sodium citrate, ethylenediamine tetraacetic acid, cyanide, thiourea, and mixtures thereof.
11. The method of Feature 10 wherein said masking agents are a mixture of sodium citrate and ethylenediamine tetraacetic acid.
12. The method of Feature 11 wherein the final concentrations of said masking agents are about 10 millimolar.
13. The method of Feature 6 wherein said solubilizing agent is a quaternary ammonium salt.
14. The method of Feature 6 wherein said solubilizing agent is ethylhexadecyldimethylammonium bromide.
15. The method of Feature 13 wherein the final concentration of the solubilizing agent is between 0.1 and 2%.
16. The method of Feature 15 wherein the final concentration of the solubilizing agent is about 1%.
17. The method of Feature 6 wherein said buffer is selected from the group consisting of 3-[cyclohexylamino]-1-propanesulfonic acid, borate, and tris(hydroxymethyl)aminomethane.

18. The method of Feature 17 wherein the final concentration of buffers is about 100 millimolar.
19. The method of Feature 6 wherein the absorbance of the reaction mixture is read in a spectrophotometer or colorimeter between a wavelength of 500 and 600 nanometers.
20. The method of Feature 19 wherein said wavelength is 570, 574, 575, 578, or 580 nanometers.
21. The method of Feature 6 wherein said biological fluid is selected from a group consisting of water, urine, blood serum, saliva, amniotic fluid, cerebrospinal fluid, sweat, stool extract, synovial fluid, tears, semen extract, sputum, and peritoneal fluid.
22. The method of Feature 6 wherein the biological fluid specimen is from a mammal.
23. A process for making a uranium-containing/metal binding complex composition which comprises the steps of (1) contacting a pyridylazo indicator dye compound with uranium-containing mixture of masking agent(s) capable of maintaining the pH at between 8 and 12 and solubilizing compound to produce uranium-containing/metal binding complex composition and (2) separating the uranium-containing/metal binding complex composition produced in step (1).
24. A diagnostic kit for the detection of uranium in biological samples comprising a uranium reagent comprising a mixture of masking agent(s); buffer agents, capable of maintaining the pH at between 8 and 12, a solubilizing compound; and a detection reagent comprising a pyridylazo indicator dye compound capable of forming a uranium-pyridylazo complex that absorbs color in the visible range which can be measured with a visible-light spectrometer or colorimeter.
25. A diagnostic kit of Feature 23 wherein the pyridylazo indicator dye compound is 2-(5-bromo-2-pyridylazo)-5-diethylaminophenol.

WORKING EXAMPLES

As an example of the applicability, human urine, spiked with varying concentrations of a uranium salt (uranyl chloride or uranyl nitrate) was assayed for uranium content by this process.

Example 1

Figure 6:
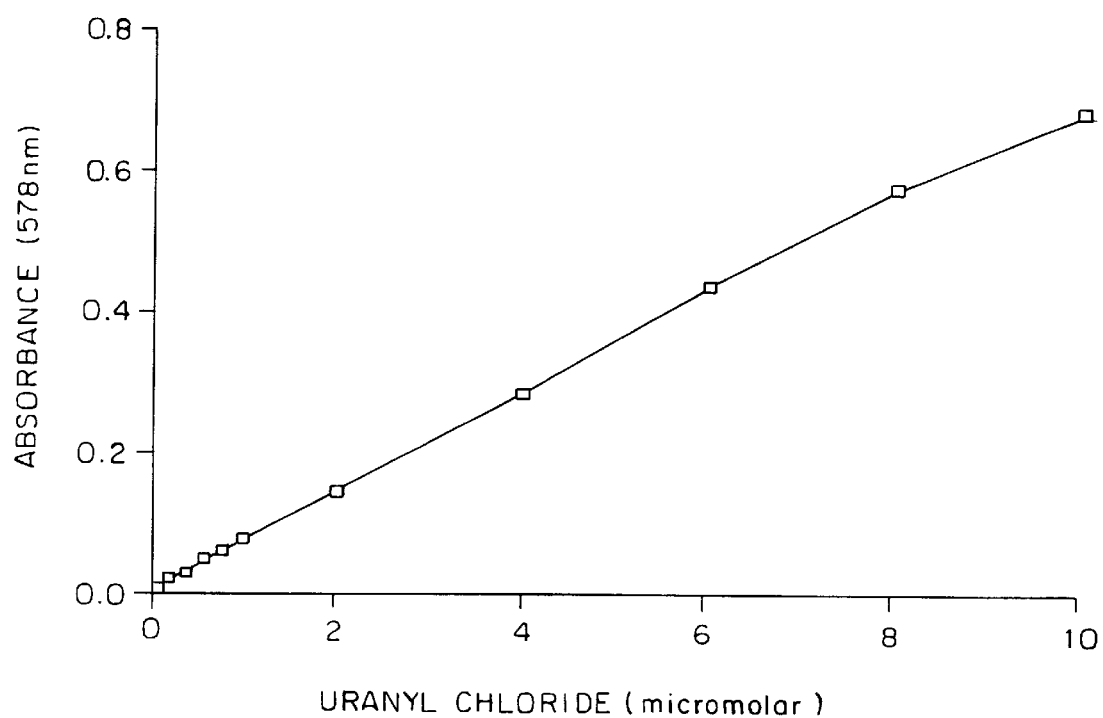
FIG. 6 shows a standard curve for the determination of uranium in urine using my process.

The following compounds were added, to the indicated final concentrations, to 1 ml of the urine sample: sodium citrate (10 mM), EDTA (10 mM), 3-[cyclohexylamino]-1-propanesulfonic acid (pH 11, 100 mM), ethylhexadecyldimethylammonium bromide (1%), and 2-(5-bromo-2-pyridylazo)-5 -diethylaminophenol (10 $\mu$M). The assay mixture was left at room temperature for 20 minutes before the absorbance, at 578 nanometers, was determined in a spectrophotometer. As shown in FIG. 6, when assayed by this process, urine containing increasing amounts of an uranium salt gives increasing absorption values. The assay shows a linear response out to 100 $\mu$M of uranium. FIG. 6 shows the response up to 10 $\mu$M of uranium in urine. Biological uranium concentrations above this are generally not encountered.

In order to determine the actual uranium concentration in a biological fluid a standard curve was constructed. A uranium salt, such as uranyl chloride or uranyl nitrate, in water produced a linear response identical to uranium in urine, when assayed using this process.

Example 2

Figure 5:
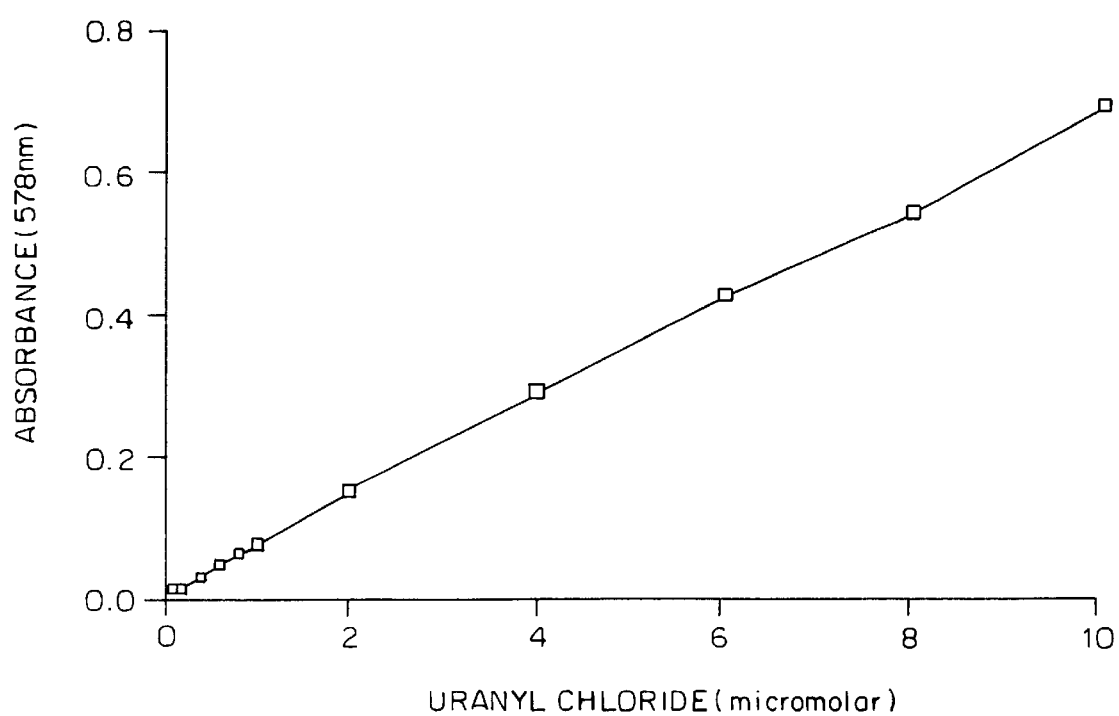
FIG. 5 shows a standard curve for the determination of uranium in water using my process.

The following compounds were added, to the final concentrations, as indicated for the urine sample in Example 1. To 1 ml of water the following compounds were added: 3-[cyclohexylamino]-1-propanesulfonic acid (pH 11, 100 mM), ethylhexadecyldimethylammonium bromide (1%), and 2-(5-bromo-2-pyridylazo)-5-diethylaminophenol (10 $\mu$M). The assay mixture was left at room temperature for 20 minutes before the absorbance, at 578 nanometers, was determined in a spectrophotometer. In this case the masking agents were not needed because the water used to establish the standard curve did not contain any endogenous metals. As seen in FIG. 5, the absorbance values obtained from the assay of uranium in water are almost identical to those obtained from the assay of uranium in urine.

In addition to the above examples, several additional factors need to be considered. Substances, such as protein, ascorbic acid, and caffeine, that might be expected to be found in certain biological fluids did not interfere with this process. Also, temperature did not affect the development of the color of the Br-PADAP-uranium complex as shown in Table 2. In fact incubation at extremely elevated temperatures (75° C.) resulted in slightly greater color development than did reactions run at room temperature (22° C.), 37° C., or 56° C. However, in order to keep the process as simple as possible to use, all manipulations were done at room temperature.

Figure 7:
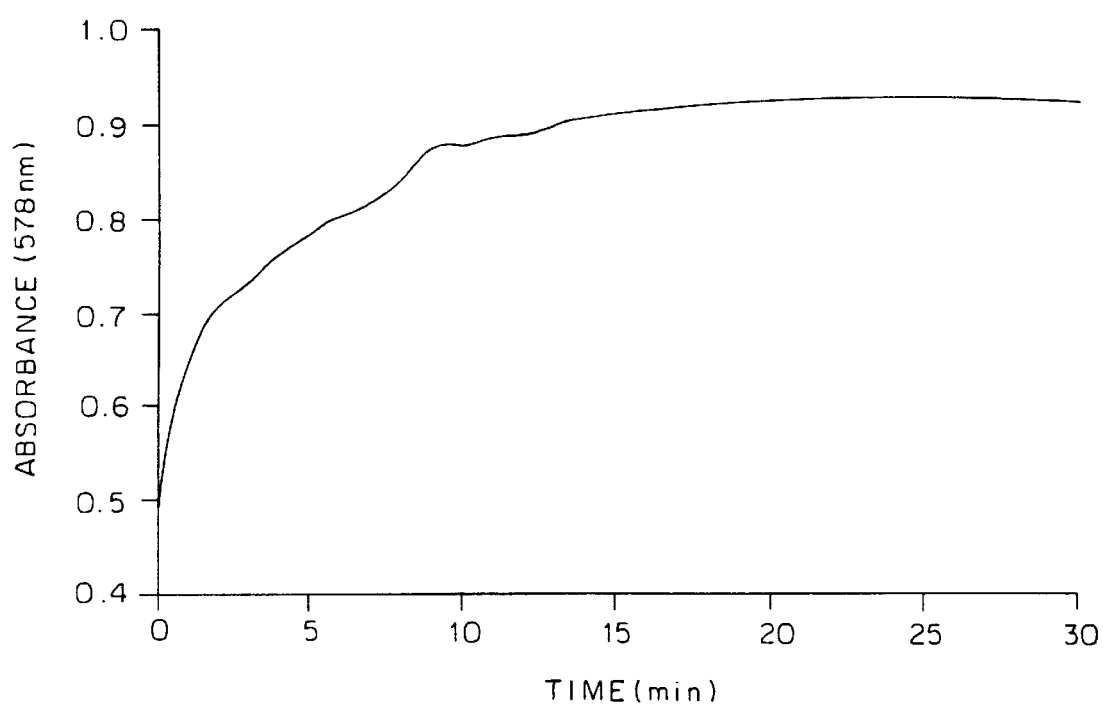
FIG. 7 shows a time course of color development for the determination of uranium in urine using my process.

As noted previously, the assay mixture was left at room temperature to allow for color development of the Br-PADAP-uranium complex. As seen in FIG. 7, when uranium-containing urine was assayed, maximum color development was attained in 15 minutes. Interestingly, when uranium-containing water samples were assayed, maximum color development was almost instantaneous. Once maximum color was attained, it was stable for periods greater then 24 hours to about 30 days. This shows that the absorbance of the assayed samples does not have to be determined immediately, but rather can be measured at the convenience of the technician.

Conclusions, Ramificaitons, and Scope

Accordingly, a skilled artist will appreciate that the production of a uranium-containing/metal binding complex compositions and its use in the practice of this invention enables the rapid, easy, and accurate determination of uranium levels in biological fluids. Furthermore, this invention has the additional advantages in that

- it provides a process for the detection of uranium, both natural or depleted, in biological fluids including urine, blood serum, saliva, amniotic fluid, cerebrospinal fluid, sweat, stool extract, synovial fluid, tears, semen extract, and peritoneal fluid;
- it provides a process for uranium determination that can be conducted with minimal manipulations;
- it provides a process for uranium determination that does not require extensive sample preparation before analysis;
- it provides a process for uranium determination that does not require the use of complicated instrumentation;
- it provides a process for uranium determination that requires only a visible-range spectrophotometer or colorimeter for instrumentation;
- it provides a process for uranium determination that can be used in a battlefield situation; and
- it provides a process for uranium determination that requires little or no technical training to conduct.

Although this specification contains many specific demonstrative illustrations, they should not be considered limitations on the scope of the invention but rather examples of the presently preferred embodiments and/or procedural

TABLE 1

Other metals tested in urine for the ability to bind Br-PADAP

| Metals that do not bind Br-PADAP | | Metals that can be masked |
|---|---|---|
| Lithium | Sodium | Manganese |
| Potassium | Rubidium | Iron |
| Cesium | Magnesium | Cobalt |
| Calcium | Barium | Nickel |
| Tantalum | Chromium | Copper |
| Molybdenum | Tungsten | Zinc |
| Silver | Gold | Cadmium |
| Mercury | Aluminum | |
| Lead | Lanthanum | |
| Cerium | Gadolinium | |

TABLE 2

Effect on the determination of uranium in urine

| Temperature | % of Room Temperature |
|---|---|
| 37° C. | 101% |
| 56° C. | 106% |
| 75° C. | 115% |

What is claimed is:

1. A metal complexing composition comprising a mixture of sodium citrate and ethylene diamine tetraacetic acid, as metal binding masking agents; a buffer capable of maintaining the pH at between at between 8 and 12; a solubilizing agent and the pyridylazo indicator dye compound, 2-(5-bromo-2-pyridylazo)-5-diethylaminophenol wherein said dye compound demonstrates a preferential reactivity with uranium to form a uranium-pyridylazo complex.

2. A method for the detection of uranium in biological fluid specimens which comprises the steps of (1) contacting the biological fluid specimens which may contain uranium with a mixture of the metal binding masking agent(s) sodium citrate and ethylene diamine tetraacetic acid; buffer agent(s), capable of maintaining the pH at between 8 and 12; and a solubilizing compound to produce a uranium-containing/metal binding complex; (2) adding a pyridylazo indicator dye compound, 2-(5-bromo-2-pyridylazo)-5-diethylaminophenol to the complexes produced in step (1); and (3) measuring the formation of uranium-pyridylazo complex with a visible-light spectrophotometer or colorimeter and (4) relating the measurements of step (3) to the presence of or concentration of uranium in biological fluid specimens.

3. A method according to claim 2 wherein the concentration of the indicator dye is between about 1 and 1000 micromolar.

4. A method according to claim 3 wherein the concentration of the indicator dye is about 10 micromolar.

5. The method of claim 2 wherein the final concentrations of said masking agents are about 10 millimolar.

6. The method of claim 2 wherein said solubilizing agent is a quaternary ammonium salt.

7. The method of claim 6 wherein the final concentration of the solubilizing agent is between 0.1 and 2%.

8. The method of claim 7 wherein the final concentration of the solubilizing agent is about 1%.

9. The method of claim 2 wherein said solubilizing agent is ethylhexadecyldimethylammonium bromide.

10. The method of claim 2 wherein said buffer is selected from the group consisting of 3-[cyclohexylamino]-1-propanesulfonic acid, borate, and tris(hydroxymethyl) aminomethane.

11. The method of claim 10 wherein the final concentration of buffers is about 100 millimolar.

12. The method of claim 2 wherein the absorbance of the reaction mixture is read in a spectrophotometer or colorimeter between a wavelength of 500 and 600 nanometers.

13. The method of claim 12 wherein said wavelength is 570, 574, 575, 578, or 580 nanometers.

14. The method of claim 2 wherein said biological fluid is selected from a group consisting of water, urine, blood serum, saliva, amniotic fluid, cerebrospinal fluid, sweat, stool extract, synovial fluid, tears, semen extract, sputum, and peritoneal fluid.

15. The method of claim 2 wherein the biological fluid specimen is from a mammal.

16. A process for making a uranium-containing/metal binding complex composition which comprises the steps of (1) contacting 2-(5-bromo-2-pyridylazo)-5-diethylaminophenol indicator dye compound with uranium-containing mixture of the masking agent(s) sodium citrate and ethylene diamine tetraacetic acid, buffer agents(s), capable of maintaining the pH at between 8 and 12; and a solubilizing compound to produce a uranium-containing/metal binding complex composition and (2) separating the uranium-containing/metal binding complex composition produced in step (1).

17. A diagnostic kit for the detection of uranium in biological samples comprising a uranium reagent comprising a mixture of sodium citrate and ethylene diamine tetraacetic acid, as masking agent(s); buffer agents, capable of maintaining the pH at between 8 and 12; a solubilizing compound; and a detection reagent comprising a pyridylazo indicator dye compound capable of forming a uranium-pyridylazo complex that absorbs color in the visible range which can be measured with a visible-light spectrometer or colorimeter.

* * * * *